United States Patent [19]

Mikkelsen

[11] Plant 4,210

[45] Feb. 7, 1978

[54] BEGONIA PLANT

[75] Inventor: James C. Mikkelsen, Ashtabula, Ohio

[73] Assignee: Mikkelsens, Inc., Ashtabula, Ohio

[21] Appl. No.: 769,690

[22] Filed: Feb. 17, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A novel begonia of the elatior type having glowing red tepals and dark green, heavy-textured leaves.

1 Drawing Figure

1

The present invention relates to a new and distinctive cultivar of begonia plant, botanically known as *Begonia elatior* (hiemalis-Fotsch) and known by the cultivar name Flambeau.

The new cultivar is a mutation of Aphrodite Red (not patented) and resulted from the irradiation of the parent Aphrodite Red. Asexual reproduction by stem and/or leaf cuttings has reproduced the unique features of the new cultivar through successive propagations.

The following characteristics distinguish the new begonia from both its parents and other begonias commercially known and used in the floriculture industry:

1. The most predominant change from the parent cultivar is the flower color which is a bright glowing red, as compared to the strawberry red color of the parent cultivar.

2. The leaf characteristics of Flambeau are also improved, the leaves having a darker green color and thicker blades with heavier texture.

3. Propagation of Flambeau by leaf cuttings is quite consistent year around whereas Aphrodite Red propagates very poorly by leaf cuttings.

4. Flower size of Flambeau is approximately 20–50% larger than Aphrodite Red and the number of tepals has also increased by similar percentages.

5. The edges of the tepals are distinctively ruffled. There is a two tone color effect in the tepals, which are darker red on the outside edges.

6. The growth habit is more vigorous and upright than Aphrodite Red; however the vigor does not prevent Flambeau from cascading for baskets.

7. Flambeau, being propagated by leaf cuttings and having inherent good vigor, is very useful for an upright flowering plant.

8. Flambeau is highly resistant, if not immune, to powdery mildew, a most important quality for commercially grown pot plant begonias.

The accompanying colored photograph illustrates the new cultivar and shows the colors as true as it is reasonably possible to obtain in a colored reproduction of this type.

The following is a detailed description of my new begonia cultivar based on plants produced under commercial practices in the greenhouses of Mikkelsens Inc., Ashtabula, Ohio. Color references are made to the Royal Horticultural Society Colour Chart except where general color terms of ordinary dictionary significance are used.

2

Parentage: A selected mutation from controlled irradiation of the cultivar Aphrodite Red.

Propagation: Is best done by leaf propagation which takes two weeks more time in the summer than Schwabenland Red, U.S. Plant Pat. No. 3,320, and 3 to 4 weeks longer in the winter. Flambeau develops adventitious shoots with greater dependability than the Elegance Series of cultivars, disclosed in my issued U.S. Plant Pat. Nos.: 3,904 (Rose Elegance); 3,905 (Elegance) and 3,913 (Red Elegance).

Rooting habit: Rooting is slower than normal for elatior begonias, being 30–35 days at 22° C; adventitious shoots initiate after rooting and take 45 to 60 additional days to develop. Roots are fibrous, dendritic.

Plant form: Plant is more upright than procumbent.

Habit of growth: Upright, compact, self branching, free growing.

Blooming habits: Flowering is produced on axillary shoots that carry a raceme type inflorescence, with flowering continuing toward apex for upwards of 2–3 months. As plant increases in terminal growth additional flowering shoots develop.

Blooming season: Flowering is indeterminate; most profuse flowering occurring during the spring season (in Ashtabula, Ohio).

Foliage: Self branching gives the impression that the quantity of foliage is quite high; leaves do not grow overly large; dark green color gives good contrast for flowers.

- *Size.*—Average, leaf size approximately 8 cm. wide by 8 cm. long.
- *Shape.*—Generally obovate.
- *Texture.*—Glabrous, crisp.
- *Margin.*—Slightly crenate to entire.
- *Color.*—Darker than yellow green 147A but lighter than green 139A.

Disease resistance: The most troublesome foliage disease of begonias, common powdery mildew, has not been seen on foliage of Flambeau to date.

Flowers:

- *Borne.*—On short pedicels which emerge along a vigorous penduncle that originates from the leaf axis, the total inflorescence being in the form of a raceme. The individual flowers are quite double and measure up to 6 cm. to 7 cm. in diameter.
- *Quantity.*—Typical for double flowering elatior type begonias.
- *Buds.*—Flat, up to 15 mm. in diameter before opening, being dark pink to light red on outside before opening.

*Tepals.*—Flowers are double; tepals are ruffle-edged, outer edges red 45C, interior of tepals toward red 52A; general overall color tone appears between red 45D and 46D.

*Reproductive organs.*—Elatior begonias are generally considered sterile. Stamens: None seen to date. Pollen: None seen to date. Styles/Ovaries: None seen to date.

I claim:

1. A new and distinct cultivar of begonia plant known by the cultivar name Flambeau and particularly characterized as to uniqueness by the combined characteristics of bright red flower color, dark green foliage having thick blades and heavy texture; consistent propagation by leaf cuttings; relatively large flower size and tepal quantity with the tepal edges being ruffled; vigorous and upright growth habit, and by its resistance to powdery mildew.

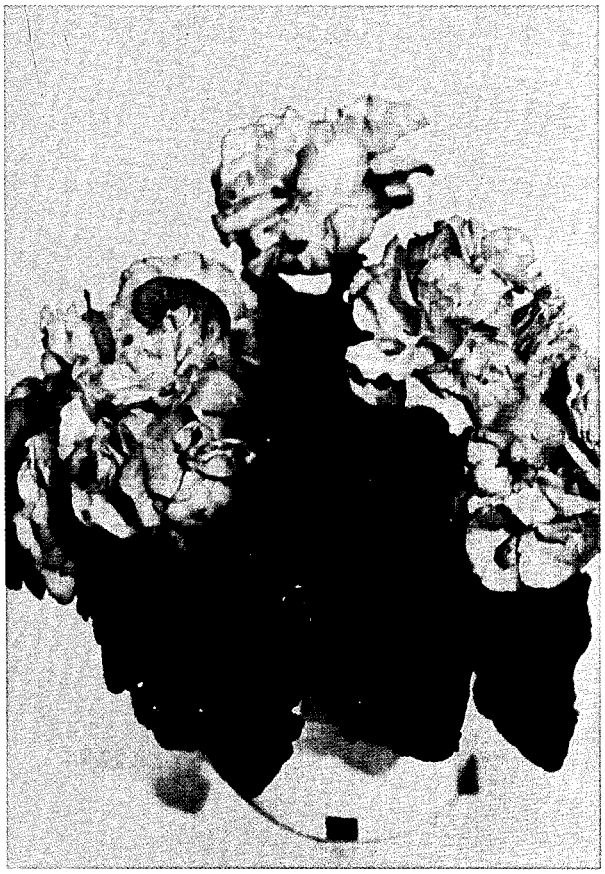

* * * * *